United States Patent [19]
Inoue et al.

[11] Patent Number: 5,883,286
[45] Date of Patent: Mar. 16, 1999

[54] PHENOL COMPOUND AND USE THEREOF

[75] Inventors: Takeshi Inoue, Fukuoka; Kazuo Nakagawa, Mie; Yoshihiro Ozaki, Osaka; Akiyoshi Onishi; Machiko Mekada, both of Yokkaichi, all of Japan

[73] Assignees: Yoshitomi Fine Chemicals, Ltd.; Mitsubishi Chemical Corporation, both of Japan

[21] Appl. No.: 860,118

[22] PCT Filed: Dec. 21, 1995

[86] PCT No.: PCT/JP95/02629

§ 371 Date: Jun. 19, 1997

§ 102(e) Date: Jun. 19, 1997

[87] PCT Pub. No.: WO96/19435

PCT Pub. Date: Jun. 27, 1996

[30] Foreign Application Priority Data

Dec. 22, 1994 [JP] Japan .................................. 6-320835

[51] Int. Cl.$^6$ ................................................. C07C 69/76
[52] U.S. Cl. ............................................ 560/73; 528/935
[58] Field of Search ................................ 560/73; 528/935

[56] References Cited

U.S. PATENT DOCUMENTS

| | | |
|---|---|---|
| 3,657,321 | 4/1972 | Steinberg et al. . |
| 4,110,306 | 8/1978 | Minagawa et al. . |
| 4,171,298 | 10/1979 | Minagawa et al. . |
| 4,199,495 | 4/1980 | Minagawa et al. . |
| 4,239,803 | 12/1980 | Ohzeki et al. . |
| 4,298,520 | 11/1981 | Minagawa et al. . |
| 4,319,051 | 3/1982 | Suenobu et al. . |
| 4,740,544 | 4/1988 | Nakahara et al. . |
| 4,759,871 | 7/1988 | Nakahara et al. . |
| 4,760,141 | 7/1988 | Nakahara et al. . |

FOREIGN PATENT DOCUMENTS

| | | |
|---|---|---|
| 38-17164 | 9/1963 | Japan . |
| 39-4469 | 4/1964 | Japan . |
| 39-4620 | 4/1964 | Japan . |
| 39-21140 | 9/1964 | Japan . |
| 42-9651 | 5/1967 | Japan . |
| 46-36601 | 10/1971 | Japan . |
| 51-21584 | 2/1976 | Japan . |
| 52-66551 | 6/1977 | Japan . |
| 52-154851 | 12/1977 | Japan . |
| 53-56239 | 5/1978 | Japan . |
| 56-40629 | 4/1981 | Japan . |
| 59-9593 | 3/1984 | Japan . |
| 62-18444 | 1/1987 | Japan . |
| 62-30134 | 6/1987 | Japan . |
| 62-156152 | 7/1987 | Japan . |
| 2-265939 | 10/1990 | Japan . |
| 951935 | 3/1964 | United Kingdom . |

*Primary Examiner*—Paul J. Killos
*Attorney, Agent, or Firm*—Wenderoth, Lind & Ponack, L.L.P.

[57] ABSTRACT

A phenol compound of the formula [1]

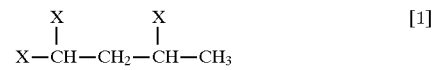

wherein each of X's is a group of the formula [2]

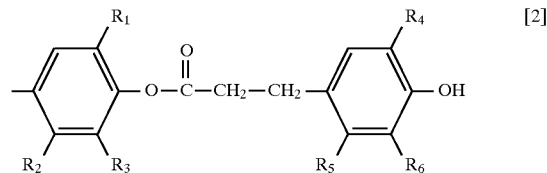

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms; a stabilizer for organic materials which comprises the compound; a composition comprising the compound and an organic material; and a composition comprising the composition and a sulfur antioxidant, and use thereof.

The compound of the present invention as used as a stabilizer for an organic material shows superior preventive effect against oxidative degradation and extremely superior resistance against degradation of an organic material in an environment involving contact with hot water for a long time, as compared to compounds conventionally used as hot water resistant antioxidants. In addition, a concurrent use of the compound of the present invention and a sulfur antioxidant brings about excellent synergistic effect to synergistically improve resistance to hot water for a long time, as compared to conventional hot water resistant antioxidants.

27 Claims, No Drawings

PHENOL COMPOUND AND USE THEREOF

TECHNICAL FIELD

The present invention relates to a novel phenol compound having a phenyl ester structure and use thereof.

More particularly, the present invention relates to a phenol compound which is useful as a stabilizer (antioxidant) for various organic materials such as synthetic macromolecular materials (e.g., polyolefin and the like), natural organic materials, cosmetics, antifreezing fluids and the like, and which shows noticeable effects when employed, particularly, in an environment involving the presence of water or hot water, and to use thereof.

BACKGROUND ART

Various organic materials inclusive of synthetic macromolecular materials such as polyolefin are associated with a problem in that they are subject to oxidation during form-processing and in use to result in degraded quality. To avoid this, various antioxidants have been heretofore developed and added to said materials for the purpose of preventing oxidative degradation.

For example, a hindered phenol compound (e.g., compounds disclosed in Japanese Patent Examined Publication Nos. 17164/1963, 4620/1964, 21140/1964, 9651/1967 and is useful for the prevention of oxidative degradation of synthetic macromolecular materials such as polyolefin in particular, and has been put to practical use.

While 1,1,3-tris-substituted butane compounds have been known as the hindered phenol compounds, for example, UK Patent No. 951935 discloses, as said compound, a compound having phenyl ester structures, which is represented by the formula

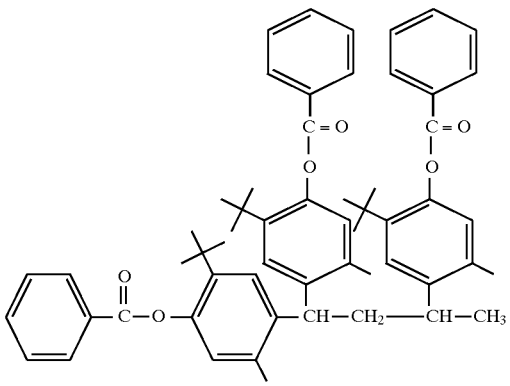

U.S. Pat. No. 4,199,495 discloses a compound having ester structures, which is represented by the formula

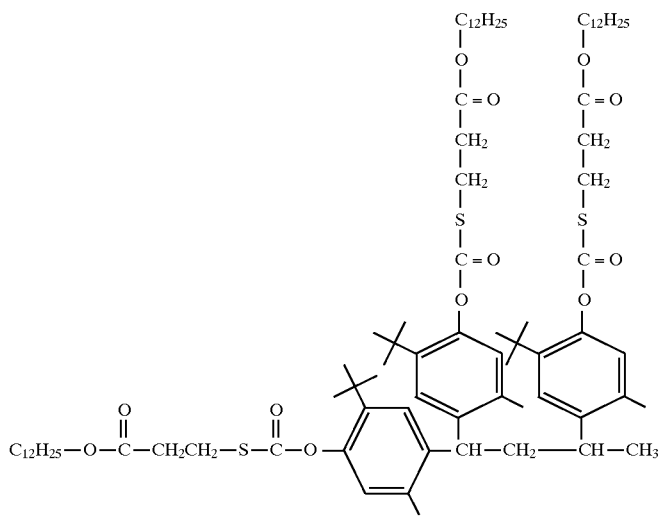

Japanese Patent Unexamined Publication No. 154851/1977 discloses a compound having ester structures, which is represented by the formula

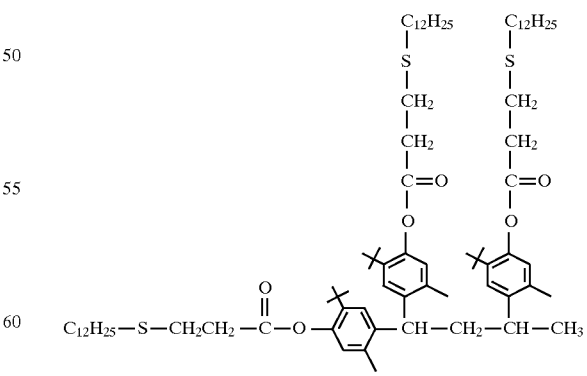

Japanese Patent Unexamined Publication No. 66551/1977 discloses a phosphite compound of the formula

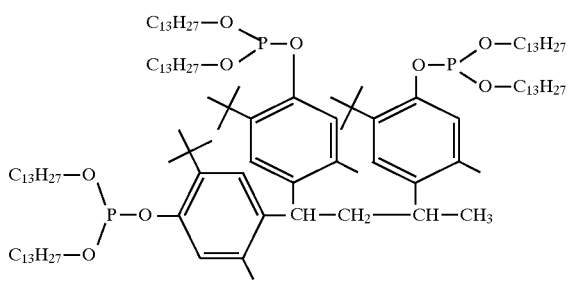

and Japanese Patent Unexamined Publication No. 56239/1978 discloses a phosphite compound of the formula

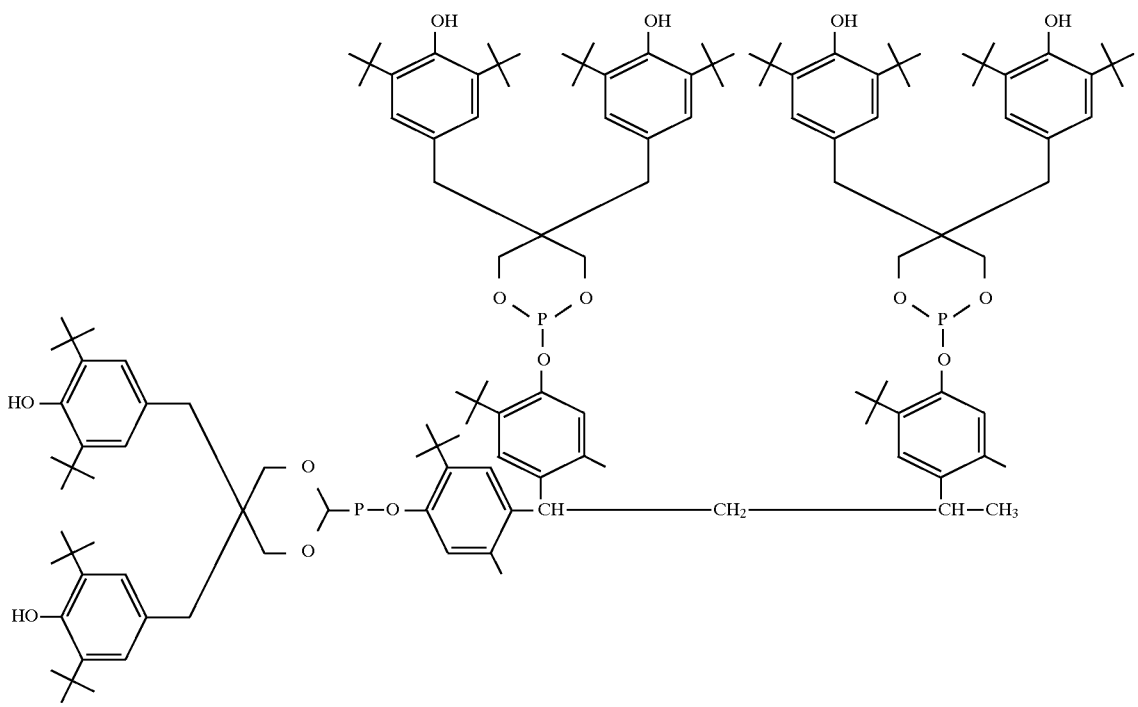

and these compounds have been known as antioxidants for synthetic macromolecular materials.

In addition, as the 1,1,3-tris-substituted butane compound, Japanese Patent Unexamined Publication No. 156152/1987 discloses a flame retardance-imparting compound of the formula

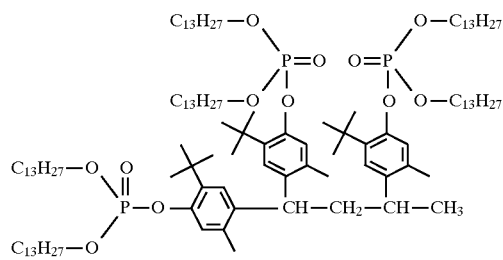

and Japanese Patent Unexamined Publication No. 18444/1987 discloses a light resistance-imparting compound of the formula

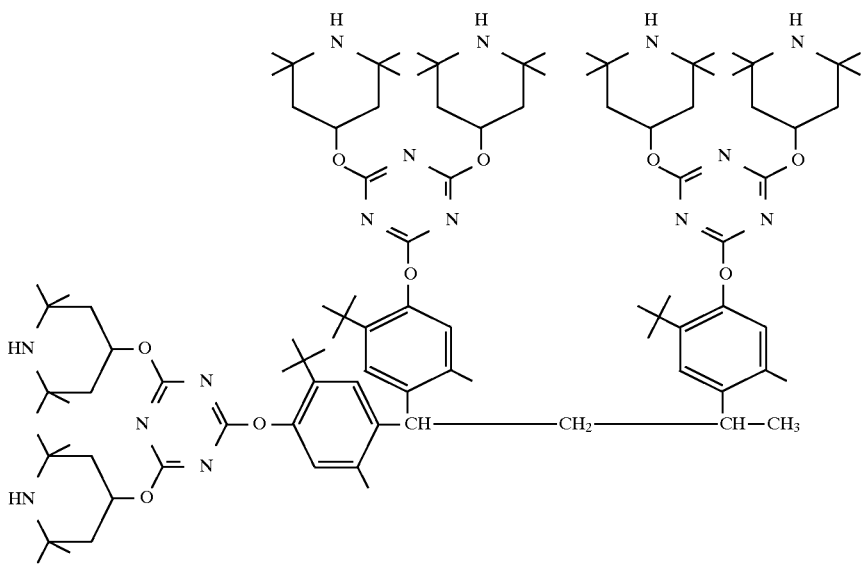

When a material stabilized with various conventional antioxidants is used in an environment involving water, however, the preventive effect thereof against oxidative degradation becomes markedly poor, and none of the conventional antioxidants has been found satisfactory.

This has been conventionally considered to be attributable to the extraction of the antioxidant with water or the extraction after hydrolysis. Hence, a material to be used in an environment involving water generally contains, for example, an antioxidant devoid of ester structure but having a high molecular weight and rigid structure, such as the composition disclosed in Japanese Patent Unexamined Publication No. 265939/1990, so that the extraction with water or hydrolysis can be prevented.

However, such an antioxidant cannot sufficiently provide resistance to oxidative degradation to a desired degree, and an antioxidant has been desired which effectively prevents oxidative degradation in an environment involving water or hot water.

DISCLOSURE OF INVENTION

The present inventors have been studying over the years on the mechanism of degradation of effects of antioxidant contained in an organic material to be used in an environment involving water. Despite the studies of the present inventors based on the mechanism of conventional oxidation that the antioxidant in an organic material is extracted with water or hydrolyzed, they failed to develop a desired antioxidant. During the course of the studies, the present inventors have found that the action of water in fact promotes oxidative denaturation of said antioxidant itself to become a compound devoid of oxidation preventive effect.

They then took note of an idea to design a compound which retains oxidation preventive potency even after oxidative denaturation by the action of water, for use along with an organic material to be used in an environment involving water, and intensively developed the studies.

As a result, the present inventors have found that a phenol compound of the following formula [1] affords, from the chemical structure of itself, a superior oxidative degradation preventive potency to organic materials, and that, even when it is used in an environment involving water or hot water and denatured thereby, the compound can still realize highly satisfactory oxidative degradation preventive potency, which resulted in the completion of the present invention. The compound of the present invention shows markedly superior retention of oxidative degradation preventive effect, since new compounds having an oxidative degradation preventive potency are successively attained despite the denaturation by water.

That is, the present invention relates to a phenol compound of the formula [1]

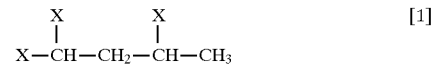

wherein each of X's is a group of the formula [2]

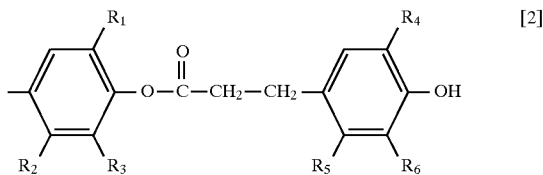

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms (hereinafter this compound [1] is also referred to as the compound of the present invention).

The present invention also relates to a stabilizer for organic materials which comprises the above-mentioned compound, a composition comprising the above-mentioned compound and an organic material, and to a composition comprising said composition and a sulfur antioxidant.

More particularly, the present invention relates to:

(1) a phenol compound of the formula [1]

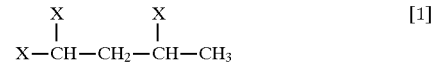

wherein each of X's is a group of the formula [2]

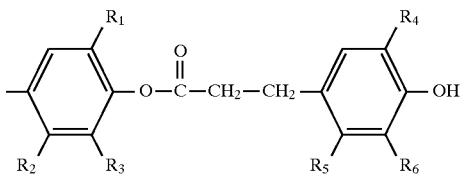

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms;

(2) the phenol compound of the above (1) wherein each of three X's in the formula [1] is the same substituent;

(3) the phenol compound of the above (1) wherein $R_6$ in the formula [2] is an alkyl having 1 to 8 carbon atoms;

(4) a stabilizer for an organic material, which comprises the compound of the above (1), (2) or (3);

(5) an organic material containing the compound of the above (1), (2) or (3);

(6) a polyolefin containing the compound of the above (1), (2) or (3);

(7) the organic material of the above (6), wherein a phenol compound of the formula [1] is contained in a proportion of 0.01–10 parts by weight relative to 100 parts by weight of the polyolefin;

(8) the organic material of the above (6), wherein the polyolefin is selected from polyethylene, polypropylene and propylene copolymer;

(9) a stabilizer for an organic material, comprising the compound of the above (1), (2) or (3) and a sulfur antioxidant;

(10) the stabilizer of the above (9), wherein the sulfur antioxidant is dilauryl thiodipropionate, dimyristyl thiodipropionate, distearyl thiodipropionate, didocosyl thiodipropionate, tetrakis[methylene (laurylthiopropionate)]methane or tetrakis[methylene (stearylthiopropionate)]methane;

(11) the stabilizer for an organic material of the above (9), wherein the sulfur antioxidant is contained in a weight ratio of 0.1–10 relative to the phenol compound of the formula [11];

(12) a method for stabilizing an organic material, which comprises adding a phenol compound of the formula [1]

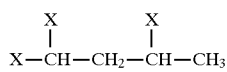

wherein each of X's is a group of the formula [2]

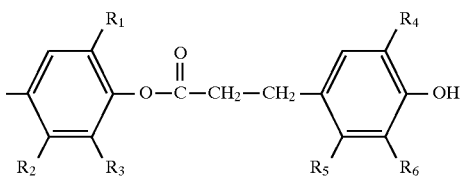

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms, to the organic material;

(13) the method for stabilizing an organic material according to the above (12), wherein each of three X's of the phenol compound of the formula [1] is the same substituent;

(14) the method for stabilizing an organic material according to the above (12), wherein, in the phenol compound, $R_6$ in the formula [2] is an alkyl having 1 to 8 carbon atoms;

(15) the method for stabilizing an organic material according to the above (12), (13) or (14), wherein the organic material is a polyolefin;

(16) the method for stabilizing an organic material according to the above (15), wherein the phenol compound of the formula [1] is contained in a proportion of 0.01–10 parts by weight relative to 100 parts by weight of the polyolefin;

(17) the method for stabilizing an organic material according to the above (15), wherein the polyolefin is selected from polyethylene, polypropylene and propylene copolymer;

(18) a composition comprising a phenol compound of the formula [1]

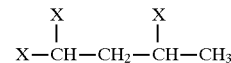

wherein each of X's is a group of the formula [2]

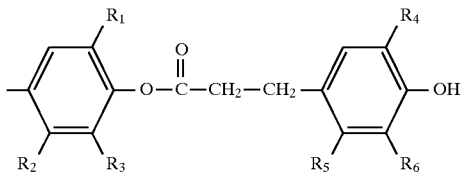

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms, and an organic material;

(19) the composition of the above (18), wherein each of three X's of the phenol compound of the formula [1] is the same substituent;

(20) the composition of the above (18), wherein, in the phenol compound, $R_6$ in the formula [2] is an alkyl having 1 to 8 carbon atoms;

(21) a stabilizer for an organic material, comprising the composition of the above (18), (19) or (20);

(22) a polyolefin composition comprising the composition of the above (18), (19) or (20);

(23) the composition of the above (22), wherein a phenol compound of the formula [1] is contained in a proportion of 0.01–10 parts by weight relative to 100 parts by weight of the polyolefin;

(24) the composition of the above (22), wherein the polyolefin is selected from polyethylene, polypropylene and propylene copolymer;

(25) the composition of the above (18), (19) or (20), further comprising a sulfur antioxidant;

(26) the composition of the above (25), wherein the sulfur antioxidant is dilauryl thiodipropionate, dimyristyl thiodipropionate, distearyl thiodipropionate, didocosyl thiodipropionate, tetrakis[methylene (laurylthiopropionate)]methane or tetrakis[methylene (stearylthiopropionate)]methane;

(27) the composition of the above (25), wherein the sulfur antioxidant is contained in a weight ratio of 0.1–10 relative to the phenol compound of the formula [1];
(28) use of a phenol compound of the formula [1]

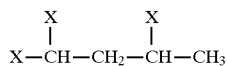

wherein each of X's is a group of the formula [2]

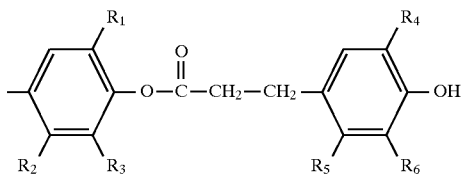

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms, in the stabilization of an organic material;
(29) the use of a phenol compound according to the above (28), wherein each of three X's of the phenol compound of the formula [1] is the same substituent;
(30) the use of a phenol compound according to the above (28), wherein, in the phenol compound, $R_6$ in the formula [2] is an alkyl having 1 to 8 carbon atoms;
(31) the use of a phenol compound according to the above (28), (29) or (30), wherein the organic material is a polyolefin;
(32) the use of a phenol compound according to the above (31), wherein a phenol compound of the formula [1] is contained in a proportion of 0.01–10 parts by weight relative to 100 parts by weight of the polyolefin; and
(33) the use of a phenol compound according to the above (31), wherein the polyolefin is selected from polyethylene, polypropylene and propylene copolymer.

Each symbol used in the present specification is explained in the following.

The alkyl at $R_1$ and $R_4$ having 1 to 8, preferably 1 to 5, carbon atoms may be linear, branched or cyclic, and is exemplified by methyl, ethyl, n-propyl, isopropyl, n-butyl, isobutyl, sec-butyl, tert-butyl, n-pentyl, isopentyl, sec-pentyl, tert-pentyl, 2-methylbutyl, n-hexyl, isohexyl, sec-hexyl, tert-hexyl, cyclohexyl, heptyl, n-octyl, isooctyl, sec-octyl, tert-octyl, 2-ethylhexyl and the like.

$R_2$, $R_3$, $R_5$ and $R_6$ include hydrogen atom and alkyl which may be linear, branched or cyclic alkyl having 1 to 8, preferably 1 to 5, carbon atoms, such as methyl, ethyl, n-propyl, isopropyl, n-butyl, isobutyl, sec-butyl, tert-butyl, n-pentyl, isopentyl, sec-pentyl, tertpentyl, 2-methylbutyl, n-hexyl, isohexyl, sec-hexyl, tert-hexyl, cyclohexyl, heptyl, n-octyl, isooctyl, sec-octyl, tert-octyl, 2-ethylhexyl and the like.

While the three X's of the compound of the formula [1] are not necessarily the same, it is generally preferable that they be the same.

Specific examples of the compound of the present invention having formula [1] include 1,1,3-tris[2-methyl-4-(3,5-di-tert-butyl-4-hydroxyphenylpropionyloxy)-5-tert-butylphenyl]butane, 1,1,3-tris[3-methyl-4-(3,5-di-tert-butyl-4-hydroxyphenylpropionyloxy)-5-tert-butylphenyl]butane, 1,1,3-tris[2-methyl-4-(3-methyl-5-tert-butyl-4-hydroxyphenylpropionyloxy)-5-tert-butylphenyl]butane, 1,1,3-tris[3-methyl-4-(3-methyl-5-tert-butyl-4-hydroxyphenylpropionyloxy)-5-tert-butylphenyl]butane and the like.

The method for producing the compound of the present invention having the formula [1] is not particularly limited, and the compound of the present invention having the formula [1] may be produced, for example, by reacting a compound of the formula

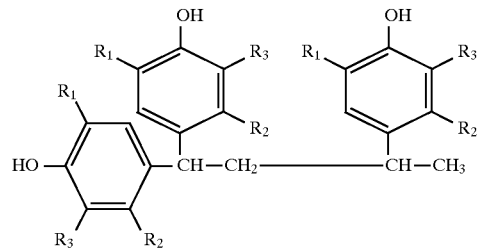

wherein each symbol is as defined above, as disclosed in Japanese Patent Examined Publication No. 4469/1964 and Japanese Patent Unexamined Publication No. 40629/1981, and a compound of the formula

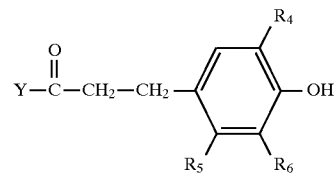

wherein Y is halogen (e.g., chlorine, bromine and iodine) and other symbols are as defined above, in the presence of an alkali.

This reaction generally proceeds in an inert solvent such as toluene.

The compound of the present invention having the formula [1] is characterized in that it is a hindered phenol compound having a hindered phenyl ester structure. In other words, in an environment involving water, the hindered phenol exerts an oxidation preventive effect during early stages of use, and when the hindered phenyl ester is denatured by the action of water during use, a new hindered phenol is produced to successively exhibit oxidative degradation preventive potency, whereby an oxidative degradation preventive effect can be retained longer than by conventional antioxidants.

The compound of the present invention having formula [1] can be used as a stabilizer for various organic materials, and is effective for preventing oxidative degradation of organic materials. The compound is particularly effective for preventing oxidative degradation of synthetic polymer which is often used in an environment involving water.

The present invention also provides an organic material containing the compound of the formula [1].

Examples of the organic material include synthetic polymer, natural organic material and the like.

The synthetic polymer is exemplified by polyolefins such as homopolymers of α-olefin having 2 to 8 carbon atoms such as polyethylene (e.g., low density polyethylene, medium density polyethylene and high density polyethylene), polypropylene and polybutene-1, α-olefin copolymers (e.g., ethylene-propylene random or block copolymer, ethylene-butene-1 random copolymer and propylene-ethylene-butene-1 random copolymer), and copolymers (e.g., maleic anhydride modified polypropylene) of poly-α-olefin and other monomer; halogen-containing polymers such as polyvinyl chloride, polyvinylidene chloride, polyvinyl fluoride, polyvinylidene fluoride and vinyl chloride-alkyl acrylate copolymer; styrene resins such as polystyrene, high impact polystyrene, ABS resin and AES resin; acrylic resins such as polyacrylate and polymethacrylate; thermoplastic polyesters such as polyethylene terephthalate and polybutylene terephthalate; polyamides such as nylon 6, nylon 66 and nylon 612; aromatic polycarbonate; polyacetal; polyethylene oxide; polyphenylene ether; polysulfone; polyurethane; unsaturated polyester resin, and mixtures thereof.

The compound of the present invention shows superior oxidative degradation preventive effect particularly when added to a polyolefin, specifically, polyethylene, polypropylene or propylene copolymer.

Examples of the natural organic material include natural high molecular substance such as cellulose, natural rubber, protein and derivatives (e.g., cellulose acetate), mineral oil, animal or plant oil, wax and the like.

The compound of the present invention exerts more superior effect particularly when combined with a sulfur antioxidant. To be specific, when the compound of the present invention and a sulfur antioxidant are used as stabilizers to be added to an organic material, a composition comprising an organic material which is more superior in stability can be obtained.

While the sulfur antioxidant is not particularly limited, preferred are dilauryl thiodipropionate, dimyristyl thiodipropionate, distearyl thiodipropionate, didocosyl thiodipropionate, tetrakis[methylene(laurylthiopropionate)] methane and tetrakis[methylene(stearylthiopropionate)] methane, which may be used alone or in combination.

When the compound of the present invention is used as a stabilizer for an organic material, the compound of the present invention is preferably added in a proportion of 0.01–10 parts by weight, more preferably 0.01–5 parts by weight, relative to 100 parts by weight of the organic material (exclusive of stabilizer), whether the compound of the present invention is used alone or concurrently with a sulfur antioxidant.

The sulfur antioxidant is preferably added in a proportion of 0.01–10 parts by weight, more preferably 0.01–5 parts by weight, relative to 100 parts by weight of the organic material (exclusive of stabilizer).

The sulfur antioxidant is added in a weight ratio (sulfur antioxidant/compound of the present invention) of 0.1–10 relative to the compound of the present invention.

When the compound of the present invention is used as a stabilizer, one or more kinds of other additives such as other phenol antioxidant, phosphorus antioxidant, light stabilizer, ultraviolet absorber, metal soap, heavy metal inactivating agent, organic tin stabilizer, epoxy compound, pigment, flame retardant, antistatic agent, lubricant, processing aid, neutralizer, neucleator, plasticizer, coloring agent, filler, foaming agent and the like, may be added as necessary to the extent that the effect of the compound of the present invention is not markedly impaired.

Said stabilizer may be added to an organic material by any method, which may be conventionally known. For example, the method may include processes of mixing an organic material and a stabilizer, kneading and extruding the same.

The present invention is explained in more detail by way of Examples and Experimental Example to which the present invention is not limited.

EXAMPLE 1

A solution of 1,1,3-tris(2-methyl-4-hydroxy-5-tert-butylphenyl)-butane (6 g), triethylamine (5 g) and toluene (30 ml) was cooled to 5° C. and a solution of 3,5-di-tert-butyl-4-hydroxyphenylpropionyl chloride (11 g) in toluene (30 ml) was added dropwise, followed by stirring at 5° C. for one hour. After the completion of the reaction, the reaction mixture was filtered. Toluene (40 ml) and water (50 ml) were added to the filtrate and washed with water. After partition, the toluene layer was concentrated and the residue was purified on a silica gel column to give a white crystalline powder of 1,1,3-tris[2-methyl-4-(3,5-di-tert-butyl-4-hydroxyphenylpropionyloxy)-5-tert-butylphenyl]butane, m.p. 101°–103° C.

The structure and physical property values thereof are shown in the following.

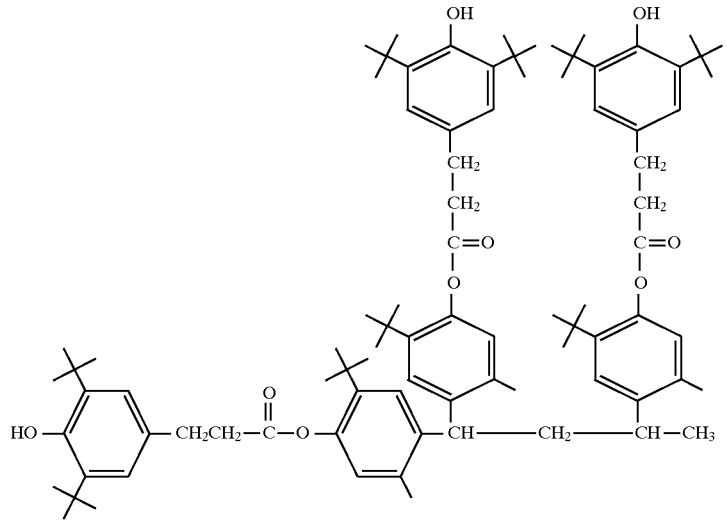

1) Elemental analysis

|     | Calculated | Found |
|-----|------------|-------|
| C % | 79.71      | 79.46 |
| H % | 9.43       | 9.47  |

2) Infrared spectroscopic analysis (KBr)

$\upsilon_{OH}$: 3600 cm$^{-1}$, $\upsilon_{C=O}$: 1726 cm$^{-1}$

3) Nuclear magnetic resonance analysis (CDCl$_3$, ppm)

| δ1.16(s, 12H)       | δ1.30(s, 9H)         |
| δ1.32(s, 11H)       | δ1.44(s, 54H)        |
| δ1.62(s, 3H)        | δ1.80(s, 3H)         |
| δ2.08(s, 4H)        | δ2.64–3.12(m, 12H)   |
| δ3.72–4.04(m, 1H)   | δ5.05(s, 3H)         |
| δ6.44–6.60(m, 3H)   | δ6.90–7.36(m, 9H)    |

EXAMPLE 2

Reaction and purification in the same manner as in Example 1 except that 1,1,3-tris(3-methyl-4-hydroxy-5-tert-butylphenyl)butane was used instead of 1,1,3-tris(2-methyl-4-hydroxy-5-tert-butylphenyl)butane of Example 1 gave a white crystalline powder of 1,1,3-tris[3-methyl-4-(3,5-di-tert-butyl-4-hydroxyphenylpropionyloxy)-5-tert-butylphenyl]-butane, m.p. 104°–113° C. The structure and physical property values thereof are shown in the following.

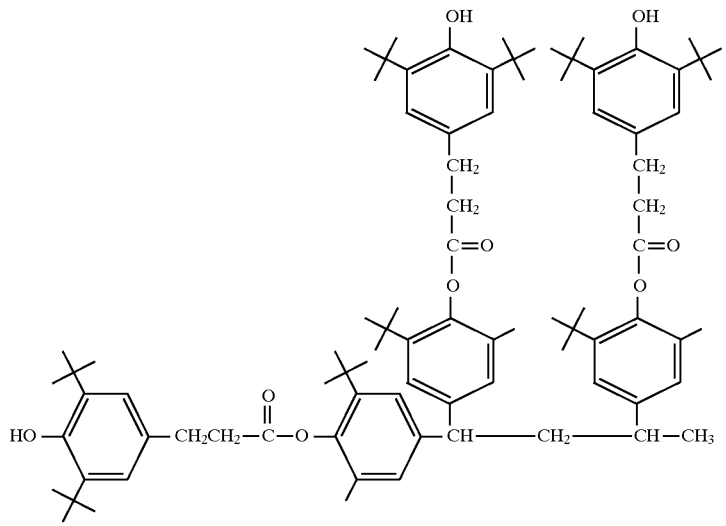

1) Elemental analysis

|     | Calculated | Found |
|-----|------------|-------|
| C % | 79.71      | 79.56 |
| H % | 9.43       | 9.27  |

2) Infrared spectroscopic analysis (KBr)

$\upsilon_{OH}$: 3600 cm$^{-1}$, $\upsilon_{C=O}$: 1725 cm$^{-1}$

3) Nuclear magnetic resonance analysis (CDCl$_3$, ppm)

| δ1.16, 1.21(d, 3H)    | δ1.24(s, 9H)         |
| δ1.25(s, 9H)          | δ1.27(s, 9H)         |
| δ1.44(s, 54H)         | δ1.91(s, 3H)         |
| δ1.93(s, 3H)          | δ1.95(s, 3H)         |
| δ2.12–2.28(m, 2H)     | δ2.45–2.52(m, 1H)    |
| δ2.85–3.10(m, 12H)    |                      |
| δ3.59, 3.62, 3.65(t, 1H) |                   |
| δ5.08(s, 3H)          | δ6.77–7.13(m, 12H)   |

EXAMPLES 3–5, COMPARATIVE EXAMPLES 1–4

A compound shown in Table 1 was added to a polypropylene powder (100 parts by weight) having an intrinsic viscosity as measured at 135° C. in tetralin of 1.9 and comprising an isotactic component by 98%, which had been polymerized by a slurry method using a Ziegler-Natta catalyst, and thoroughly mixed in a mixer. The mixture was melt-kneaded in and extruded in strands from an extruder at a cylinder temperature of 260° C., L/D=20, output diameter 20 mm, and cut to give pellets of an organic material containing a stabilizer.

TABLE 1

|                       | compound added              | amount added (part by weight) |
|-----------------------|-----------------------------|-------------------------------|
| Example 3             | compound of Example 1       | 0.2                           |
| Example 4             | compound of Example 2       | 0.2                           |
| Example 5             | compound of Example 1       | 0.5                           |
|                       | dimyristyl thiodipropionate | 0.5                           |
| Comparative Example 1 | compound A                  | 0.2                           |
| Comparative Example 2 | compound A                  | 0.6                           |
| Comparative           | compound B                  | 0.2                           |

TABLE 1-continued

| compound added | | amount added (part by weight) |
|---|---|---|
| Example 3 Comparative Example 4 | compound A dimyristyl thiodipropionate | 0.5 0.5 | compound A: 1,3,5-trimethyl-2,4,6-tris(3,5-di-tert-butyl-4-hydroxy-benzyl)benzene (manufactured by Ciba-Geigy Ltd., trademark IRGANOX 1330)
compound B: tetrakis[methylene-3-(3,5-di-tert-butyl-4-hydroxyphenyl)-propionate]methane (manufactured by Ciba-Geigy Ltd., trademark IRGANOX 1010)

EXPERIMENTAL EXAMPLE

The pellets (stabilizer-containing organic material) obtained in the above-mentioned Examples and Comparative Examples were compression-molded and formed at 230° C. into a sheet having a thickness of 0.5 mm, from which 50 mm×20 mm test pieces were cut out.

The obtained test pieces were subjected to a hot water resistance test. That is, the test pieces were immersed in distilled water at 90° C. for a predetermined time (0, 1000, 3000, 5000 hr) and placed in a Geer oven at 150° C. The time necessary for the test pieces to become brittle (life in oven) was measured. The results are shown in Table 2.

TABLE 2

Life in oven at 150° C. after immersion in distilled water at 90° C.

| | Immersion time (hr) | | | |
|---|---|---|---|---|
| | 0 | 1000 | 3000 | 5000 |
| Example 3 | 700 | 570 | 510 | 470 |
| Example 4 | 720 | 600 | 530 | 490 |
| Example 5 | 1780 | 1500 | 1260 | 1230 |
| Comparative Example 1 | 300 | 240 | 100 | 30 |
| Comparative Example 2 | 730 | 630 | 420 | 110 |
| Comparative Example 3 | 800 | 610 | 460 | 350 |
| Comparative Example 4 | 1280 | 1080 | 860 | 750 |

From the results of Table 2, it is evident that the polypropylene moldings containing the phenol compound of the present invention were superior in durability after keeping same in hot water for an extended period of time.

To summarize, when compared to the case where known antioxidants shown in Comparative Examples 1 and 3 were added in the same amount, the polymers of Examples 1 and 2 of the present invention apparently take longer to become brittle.

The difference in effects is remarkable when Example 5 in which a sulfur antioxidant was concurrently used and Comparative Example 4 are compared.

INDUSTRIAL APPLICABILITY

The compound of the present invention as used as a stabilizer for an organic material shows superior preventive effect against oxidative degradation and extremely superior resistance against degradation of an organic material in an environment involving contact with hot water for a long time, as compared to compounds conventionally used as hot water resistant antioxidants. In addition, a concurrent use of the compound of the present invention and a sulfur antioxidant brings about excellent synergistic effect to synergistically improve resistance to hot water for a long time, as compared to conventional hot water resistant antioxidants.

What is claimed is:

1. A phenol compound of the formula [1]

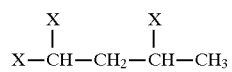

wherein each of X's is a group of the formula [2]

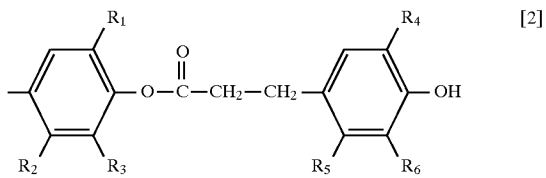

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms.

2. The phenol compound of claim 1, wherein each of three X's in the formula [1] is the same substituent.

3. The phenol compound of claim 1, wherein R6 in the formula [2] is an alkyl having 1 to 8 carbon atoms.

4. A stabilizer for an organic material, which comprises the compound of any one of claim 1, claim 2 and claim 3.

5. An organic material containing the compound of any one of claim 1, claim 2 and claim 3.

6. A polyolefin containing the compound of any one of claim 1, claim 2 and claim 3.

7. The organic material of claim 6, wherein a phenol compound of the formula [1] is contained in a proportion of 0.01–10 parts by weight relative to 100 parts by weight of the polyolefin.

8. The organic material of claim 6, wherein the polyolefin is selected from the group consisting of polyethylene, polypropylene and propylene copolymer.

9. A stabilizer for an organic material, comprising the compound of any one of claim 1, claim 2 and claim 3, and a sulfur antioxidant.

10. The stabilizer of claim 9, wherein the sulfur antioxidant is selected from the group consisting of dilauryl thiodipropionate, dimyristyl thiodipropionate, distearyl thiodipropionate, didocosyl thiodipropionate, tetrakis[methylene(laurylthiopropionate)]methane and tetrakis[methylene(stearylthiopropionate)]methane.

11. The stabilizer for an organic material of claim 9, wherein the sulfur antioxidant is contained in a weight ratio of 0.1–10 relative to the phenol compound of the formula [1].

12. A method for stabilizing an organic material, which comprises adding a phenol compound of the formula [1]

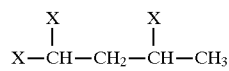

[1]

wherein each of X's is a group of the formula [2]

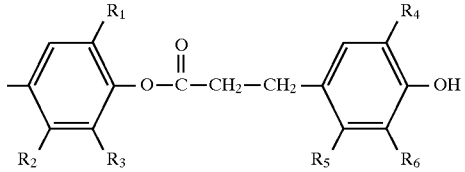

[2]

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms, to the organic material.

13. The method for stabilizing an organic material according to claim 12, wherein each of three X's of the phenol compound of the formula [1] is the same substituent.

14. The method for stabilizing an organic material according to claim 12, wherein, in the phenol compound, $R_6$ in the formula [2] is an alkyl having 1to 8 carbon atoms.

15. The method for stabilizing an organic material according to any one of claim 12, claim 13 and claim 14, wherein the organic material is a polyolefin.

16. The method for stabilizing an organic material according to claim 15, wherein the phenol compound of the formula [1] is contained in a proportion of 0.01–10 parts by weight relative to 100 parts by weight of the polyolefin.

17. The method for stabilizing an organic material according to claim 15, wherein the polyolefin is selected from the group consisting of polyethylene, polypropylene and propylene copolymer.

18. A composition comprising a phenol compound of the formula [1]

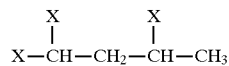

[1]

wherein each of X's is a group of the formula [2]

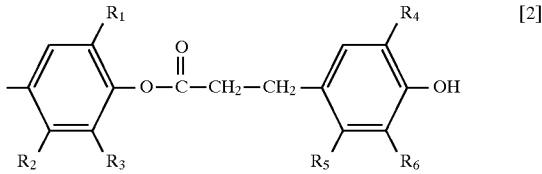

[2]

wherein $R_1$ and $R_4$ are the same or different and each is an alkyl having 1 to 8 carbon atoms, and $R_2$, $R_3$, $R_5$ and $R_6$ are the same or different and each is a hydrogen atom or an alkyl having 1 to 8 carbon atoms, and an organic material.

19. The composition of claim 18, wherein each of three X's of the phenol compound of the formula [1] is the same substituent.

20. The composition of claim 18, wherein, in the phenol compound, $R_6$ in the formula [2] is an alkyl having 1 to 8 carbon atoms.

21. A stabilizer for an organic material, comprising the composition of any one of claim 18, claim 19 and claim 20.

22. A polyolefin composition comprising the composition of any one of claim 18, claim 19 and claim 20.

23. The composition of claim 22, wherein a phenol compound of the formula [1] is contained in a proportion of 0.01–10 parts by weight relative to 100 parts by weight of the polyolefin.

24. The composition of claim 22, wherein the polyolefin is selected from the group consisting of polyethylene, polypropylene and propylene copolymer.

25. The composition of any one of claim 18, claim 19 and claim 20, further comprising a sulfur antioxidant.

26. The composition of claim 25, wherein the sulfur antioxidant is selected from the group consisting of dilauryl thiodipropionate, dimyristyl thiodipropionate, distearyl thiodipropionate, didocosyl thiodipropionate, tetrakis [methylene(laurylthiopropionate)]methane and tetrakis [methylene(stearylthiopropionate)]methane.

27. The composition of claim 25, wherein the sulfur antioxidant is contained in a weight ratio of 0.1–10 relative to the phenol compound of the formula [1].

* * * * *